US010368941B2

(12) United States Patent
Webster et al.

(10) Patent No.: US 10,368,941 B2
(45) Date of Patent: Aug. 6, 2019

(54) SYSTEMS AND METHODS FOR DELIVERING ENERGY TO PASSAGEWAYS IN A PATIENT

(75) Inventors: Noah Webster, San Francisco, CA (US); Timothy Dalbec, Saratoga, CA (US); Huy Phan, Santa Clara, CA (US); William Wizeman, Menlo Park, CA (US); William Evans, San Francisco, CA (US); Matthew Presta, San Mateo, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1304 days.

(21) Appl. No.: 13/540,091

(22) Filed: Jul. 2, 2012

(65) Prior Publication Data

US 2012/0330299 A1 Dec. 27, 2012

Related U.S. Application Data

(63) Continuation of application No. 11/777,225, filed on Jul. 12, 2007, now Pat. No. 8,235,983.

(51) Int. Cl.
*A61B 17/00* (2006.01)
*A61B 18/00* (2006.01)
(Continued)

(52) U.S. Cl.
CPC ...... *A61B 18/1492* (2013.01); *A61B 18/0206* (2013.01); *A61B 18/082* (2013.01);
(Continued)

(58) Field of Classification Search
CPC .............. A61B 2018/0091; A61B 2018/00267
See application file for complete search history.

(56) References Cited

U.S. PATENT DOCUMENTS 1,155,169 A 9/1915 Starkweather
1,207,479 A 12/1916 Bisgaard
(Continued)

FOREIGN PATENT DOCUMENTS

CN 1078595 A 11/1993
EP 189329 A3 6/1987
(Continued)

OTHER PUBLICATIONS

International Search Report and Written Opinion dated Oct. 1, 2008, International Application No. PCT/US2008/065867 (8 pages).
(Continued)

Primary Examiner — Kaitlyn E Smith
(74) Attorney, Agent, or Firm — Bookoff McAndrews, PLLC

(57) ABSTRACT

Systems and methods for delivering energy to passageways in a patient, such as airways in the lung of a patient for treating asthma. One embodiment of a method for delivering energy to a passageway comprises positioning an access device in a lung airway of a patient and advancing an elongated body of a treatment device along the access device until an energy delivery unit at a distal portion of the elongated body projects from the access device. The method can further include expanding the energy delivery unit such that energy delivery elements contact a sidewall of the airway and activating an energy supply coupled to the treatment device such that energy is delivered to the sidewall of the airway. A single person physically operates both the access device and the treatment device while expanding the energy delivery unit and activating the energy supply.

17 Claims, 6 Drawing Sheets

(51) Int. Cl.
*A61B 18/02* (2006.01)
*A61B 18/08* (2006.01)
*A61B 18/14* (2006.01)
*A61B 18/18* (2006.01)
*A61B 18/20* (2006.01)

(52) U.S. Cl.
CPC ........... *A61B 18/1815* (2013.01); *A61B 18/20* (2013.01); *A61B 2017/00092* (2013.01); *A61B 2018/0016* (2013.01); *A61B 2018/0091* (2013.01); *A61B 2018/00214* (2013.01); *A61B 2018/00267* (2013.01); *A61B 2018/00541* (2013.01); *A61B 2018/00577* (2013.01); *A61B 2018/1465* (2013.01); *A61B 2018/1467* (2013.01); *A61B 2018/1475* (2013.01)

(56) References Cited

U.S. PATENT DOCUMENTS

| | | | |
|---|---|---|---|
| 2,072,346 A | 3/1937 | Smith | |
| 3,320,957 A | 5/1967 | Sokolik | |
| 3,568,659 A | 3/1971 | Karnegis | |
| 3,667,476 A | 6/1972 | Muller | |
| 3,692,029 A | 9/1972 | Adair | |
| 4,461,283 A | 7/1984 | Doi | |
| 4,503,855 A | 3/1985 | Maslanka | |
| 4,522,212 A | 6/1985 | Gelinas et al. | |
| 4,565,200 A | 1/1986 | Cosman | |
| 4,567,882 A | 2/1986 | Heller | |
| 4,584,998 A | 4/1986 | McGrail | |
| 4,612,934 A | 9/1986 | Borkan | |
| 4,643,186 A | 2/1987 | Rosen et al. | |
| 4,674,497 A | 6/1987 | Ogasawara | |
| 4,706,688 A | 11/1987 | Don Michael et al. | |
| 4,709,698 A | 12/1987 | Johnston et al. | |
| 4,799,479 A | 1/1989 | Spears | |
| 4,802,492 A | 2/1989 | Grunstein | |
| 4,825,871 A | 5/1989 | Cansell | |
| 4,827,935 A | 5/1989 | Geddes et al. | |
| 4,862,886 A | 9/1989 | Clarke et al. | |
| 4,920,978 A | 5/1990 | Colvin | |
| 4,927,427 A * | 5/1990 | Kriauciunas et al. | 606/128 |
| 4,955,377 A | 9/1990 | Lennox et al. | |
| 4,967,765 A | 11/1990 | Turner et al. | |
| 4,976,709 A | 12/1990 | Sand | |
| 5,010,892 A | 4/1991 | Colvin et al. | |
| 5,019,075 A | 5/1991 | Spears et al. | |
| 5,053,033 A | 10/1991 | Clarke | |
| 5,056,519 A | 10/1991 | Vince | |
| 5,074,860 A | 12/1991 | Gregory et al. | |
| 5,078,716 A | 1/1992 | Doll | |
| 5,084,044 A | 1/1992 | Quint | |
| 5,096,916 A | 3/1992 | Skupin | |
| 5,100,388 A | 3/1992 | Behl et al. | |
| 5,100,423 A | 3/1992 | Fearnot | |
| 5,103,804 A | 4/1992 | Abele et al. | |
| 5,106,360 A | 4/1992 | Ishiwara et al. | |
| 5,116,864 A | 5/1992 | March et al. | |
| 5,117,828 A | 6/1992 | Metzger et al. | |
| 5,135,517 A | 8/1992 | McCoy | |
| 5,152,286 A | 10/1992 | Sitko et al. | |
| 5,170,803 A | 12/1992 | Hewson et al. | |
| 5,174,288 A | 12/1992 | Bardy et al. | |
| 5,188,602 A | 2/1993 | Nichols | |
| 5,191,883 A | 3/1993 | Lennox et al. | |
| 5,215,103 A | 6/1993 | Desai | |
| 5,254,088 A | 10/1993 | Lundquist et al. | |
| 5,255,678 A | 10/1993 | Deslauriers et al. | |
| 5,255,679 A | 10/1993 | Imran | |
| 5,265,604 A | 11/1993 | Vince | |
| 5,269,758 A | 12/1993 | Taheri | |
| 5,281,218 A | 1/1994 | Imran | |
| 5,292,331 A | 3/1994 | Boneau | |
| 5,293,869 A | 3/1994 | Edwards et al. | |
| 5,309,910 A | 5/1994 | Edwards et al. | |
| 5,311,866 A | 5/1994 | Kagan et al. | |
| 5,313,943 A | 5/1994 | Houser et al. | |
| 5,322,503 A | 6/1994 | Desai | |
| 5,324,284 A | 6/1994 | Imran | |
| 5,343,936 A | 9/1994 | Beatenbough et al. | |
| 5,345,936 A * | 9/1994 | Pomeranz et al. | 600/374 |
| 5,366,443 A | 11/1994 | Eggers et al. | |
| 5,368,591 A | 11/1994 | Lennox et al. | |
| 5,370,644 A | 12/1994 | Langberg | |
| 5,370,679 A | 12/1994 | Atlee, III | |
| 5,374,287 A | 12/1994 | Rubin | |
| 5,383,917 A | 1/1995 | Desai et al. | |
| 5,389,098 A | 2/1995 | Tsu Ruta et al. | |
| 5,394,880 A | 3/1995 | Atlee, III | |
| 5,396,887 A | 3/1995 | Imran | |
| 5,400,783 A | 3/1995 | Pomeranz et al. | |
| 5,409,469 A | 4/1995 | Schaerf | |
| 5,411,025 A | 5/1995 | Webster, Jr. | |
| 5,415,166 A | 5/1995 | Imran | |
| 5,415,656 A | 5/1995 | Tihon et al. | |
| 5,417,687 A | 5/1995 | Nardella et al. | |
| 5,423,744 A | 6/1995 | Gencheff et al. | |
| 5,423,811 A | 6/1995 | Imran et al. | |
| 5,425,703 A | 6/1995 | Feiring | |
| 5,431,696 A | 7/1995 | Atlee, III | |
| 5,433,730 A | 7/1995 | Alt | |
| 5,443,470 A | 8/1995 | Stern et al. | |
| 5,454,782 A | 10/1995 | Perkins | |
| 5,456,667 A | 10/1995 | Ham et al. | |
| 5,456,684 A | 10/1995 | Schmidt et al. | |
| 5,458,596 A | 10/1995 | Lax et al. | |
| 5,458,598 A * | 10/1995 | Feinberg et al. | 606/52 |
| 5,464,404 A | 11/1995 | Abela et al. | |
| 5,465,717 A | 11/1995 | Imran et al. | |
| 5,471,982 A | 12/1995 | Edwards et al. | |
| 5,474,530 A | 12/1995 | Passafaro et al. | |
| 5,478,309 A | 12/1995 | Sweezer et al. | |
| 5,478,350 A * | 12/1995 | Kratsch et al. | 606/205 |
| 5,496,271 A | 3/1996 | Burton et al. | |
| 5,496,311 A | 3/1996 | Abele et al. | |
| 5,500,011 A | 3/1996 | Desai | |
| 5,505,728 A | 4/1996 | Ellman et al. | |
| 5,505,730 A | 4/1996 | Edwards | |
| 5,509,411 A | 4/1996 | Littmann et al. | |
| 5,509,419 A | 4/1996 | Edwards et al. | |
| 5,522,862 A | 6/1996 | Testerman et al. | |
| 5,531,779 A | 7/1996 | Dahl et al. | |
| 5,540,681 A | 7/1996 | Strul et al. | |
| 5,545,161 A | 8/1996 | Imran | |
| 5,545,193 A | 8/1996 | Fleischman et al. | |
| 5,547,469 A | 8/1996 | Rowland et al. | |
| 5,549,559 A | 8/1996 | Eshel | |
| 5,549,655 A | 8/1996 | Erickson | |
| 5,549,661 A * | 8/1996 | Kordis et al. | 607/99 |
| RE35,330 E | 9/1996 | Malone et al. | |
| 5,558,073 A | 9/1996 | Pomeranz et al. | |
| 5,562,608 A | 10/1996 | Sekins et al. | |
| 5,562,619 A | 10/1996 | Mirarchi et al. | |
| 5,571,088 A | 11/1996 | Lennox et al. | |
| 5,575,810 A * | 11/1996 | Swanson et al. | 607/99 |
| 5,578,067 A | 11/1996 | Ekwall et al. | |
| 5,582,609 A | 12/1996 | Swanson et al. | |
| 5,588,432 A | 12/1996 | Crowley | |
| 5,595,183 A | 1/1997 | Swanson et al. | |
| 5,598,848 A | 2/1997 | Swanson et al. | |
| 5,599,345 A | 2/1997 | Edwards et al. | |
| 5,601,088 A | 2/1997 | Swanson et al. | |
| 5,605,157 A | 2/1997 | Panescu et al. | |
| 5,607,419 A | 3/1997 | Amplatz et al. | |
| 5,607,462 A | 3/1997 | Imran | |
| 5,620,438 A | 4/1997 | Amplatz et al. | |
| 5,623,940 A | 4/1997 | Daikuzono | |
| 5,624,439 A | 4/1997 | Edwards et al. | |
| 5,626,618 A | 5/1997 | Ward et al. | |
| 5,630,425 A | 5/1997 | Panescu et al. | |
| 5,630,794 A | 5/1997 | Lax et al. | |
| 5,634,471 A | 6/1997 | Fairfax et al. | |
| 5,647,870 A | 7/1997 | Kordis et al. | |
| 5,678,535 A | 10/1997 | DiMarco | |

(56) References Cited

U.S. PATENT DOCUMENTS

| | | | |
|---|---|---|---|
| 5,680,860 | A | 10/1997 | Imran |
| 5,681,280 | A | 10/1997 | Rusk et al. |
| 5,681,308 | A | 10/1997 | Edwards et al. |
| 5,693,078 | A | 12/1997 | Desai et al. |
| 5,699,799 | A | 12/1997 | Xu et al. |
| 5,707,352 | A | 1/1998 | Sekins et al. |
| 5,722,401 | A | 3/1998 | Pietroski et al. |
| 5,722,403 | A | 3/1998 | McGee et al. |
| 5,722,416 | A | 3/1998 | Swanson et al. |
| 5,725,525 | A | 3/1998 | Kordis |
| 5,728,094 | A | 3/1998 | Edwards |
| 5,730,128 | A | 3/1998 | Pomeranz et al. |
| 5,730,726 | A | 3/1998 | Klingenstein |
| 5,730,741 | A | 3/1998 | Horzewski et al. |
| 5,735,849 | A * | 4/1998 | Baden et al. .................. 606/51 |
| 5,740,808 | A | 4/1998 | Panescu et al. |
| 5,752,518 | A | 5/1998 | McGee et al. |
| 5,755,753 | A | 5/1998 | Knowlton |
| 5,759,158 | A | 6/1998 | Swanson |
| 5,769,846 | A | 6/1998 | Edwards et al. |
| 5,769,880 | A * | 6/1998 | Truckai .............. A61B 18/1485 604/114 |
| 5,772,590 | A | 6/1998 | Webster, Jr. |
| 5,779,669 | A | 7/1998 | Haissaguerre et al. |
| 5,779,698 | A | 7/1998 | Clayman et al. |
| 5,782,239 | A | 7/1998 | Webster, Jr. |
| 5,782,795 | A | 7/1998 | Bays |
| 5,782,827 | A | 7/1998 | Gough et al. |
| 5,782,844 | A * | 7/1998 | Yoon et al. .................. 606/139 |
| 5,782,899 | A | 7/1998 | Imran |
| 5,792,064 | A | 8/1998 | Panescu et al. |
| 5,795,303 | A | 8/1998 | Swanson et al. |
| 5,807,306 | A | 9/1998 | Shapland et al. |
| 5,807,393 | A * | 9/1998 | Williamson et al. ........... 606/32 |
| 5,810,807 | A | 9/1998 | Ganz et al. |
| 5,814,029 | A | 9/1998 | Hassett |
| 5,823,189 | A | 10/1998 | Kordis |
| 5,824,359 | A | 10/1998 | Khan et al. |
| 5,827,277 | A | 10/1998 | Edwards |
| 5,833,632 | A | 11/1998 | Jacobsen et al. |
| 5,836,946 | A | 11/1998 | Diaz et al. |
| 5,836,947 | A | 11/1998 | Fleischman et al. |
| 5,837,001 | A | 11/1998 | Mackey |
| 5,843,075 | A | 12/1998 | Taylor |
| 5,843,077 | A | 12/1998 | Edwards |
| 5,846,238 | A | 12/1998 | Jackson et al. |
| 5,848,969 | A | 12/1998 | Panescu et al. |
| 5,848,972 | A | 12/1998 | Triedman et al. |
| 5,849,011 | A | 12/1998 | Jones et al. |
| 5,855,577 | A | 1/1999 | Murphy-Chutorian et al. |
| 5,860,974 | A | 1/1999 | Abele |
| 5,863,291 | A | 1/1999 | Schaer |
| 5,865,791 | A | 2/1999 | Whayne et al. |
| 5,868,740 | A | 2/1999 | Leveen et al. |
| 5,871,443 | A | 2/1999 | Edwards et al. |
| 5,871,523 | A | 2/1999 | Fleischman et al. |
| 5,873,865 | A | 2/1999 | Horzewski et al. |
| 5,876,340 | A | 3/1999 | Tu et al. |
| 5,876,399 | A | 3/1999 | Chia et al. |
| 5,881,727 | A | 3/1999 | Edwards |
| 5,882,346 | A | 3/1999 | Pomeranz et al. |
| 5,891,135 | A | 4/1999 | Jackson et al. |
| 5,891,136 | A | 4/1999 | McGee et al. |
| 5,891,138 | A | 4/1999 | Tu et al. |
| 5,893,847 | A | 4/1999 | Kordis |
| 5,897,554 | A | 4/1999 | Chia et al. |
| 5,899,882 | A | 5/1999 | Waksman et al. |
| 5,904,651 | A | 5/1999 | Swanson et al. |
| 5,904,711 | A | 5/1999 | Flom et al. |
| 5,906,636 | A | 5/1999 | Casscells, III et al. |
| 5,908,445 | A | 6/1999 | Whayne et al. |
| 5,908,446 | A | 6/1999 | Imran |
| 5,911,218 | A | 6/1999 | DiMarco |
| 5,916,235 | A | 6/1999 | Guglielmi |
| 5,919,147 | A | 7/1999 | Jain |
| 5,921,999 | A | 7/1999 | Dileo |
| 5,928,228 | A | 7/1999 | Kordis et al. |
| 5,935,079 | A | 8/1999 | Swanson et al. |
| 5,941,869 | A | 8/1999 | Patterson et al. |
| 5,951,494 | A | 9/1999 | Wang et al. |
| 5,954,661 | A | 9/1999 | Greenspon et al. |
| 5,954,662 | A | 9/1999 | Swanson et al. |
| 5,954,717 | A | 9/1999 | Behl et al. |
| 5,957,842 | A | 9/1999 | Littmann et al. |
| 5,957,961 | A | 9/1999 | Maguire et al. |
| 5,964,753 | A | 10/1999 | Edwards |
| 5,964,756 | A * | 10/1999 | McGaffigan et al. ........... 606/41 |
| 5,964,796 | A | 10/1999 | Imran |
| 5,968,087 | A | 10/1999 | Hess et al. |
| 5,971,983 | A | 10/1999 | Lesh |
| 5,972,026 | A | 10/1999 | Laufer et al. |
| 5,979,456 | A | 11/1999 | Magovern |
| 5,980,519 | A * | 11/1999 | Hahnen et al. ................. 606/49 |
| 5,980,563 | A | 11/1999 | Tu et al. |
| 5,991,650 | A | 11/1999 | Swanson et al. |
| 5,992,419 | A | 11/1999 | Sterzer et al. |
| 5,993,462 | A | 11/1999 | Pomeranz et al. |
| 5,997,534 | A | 12/1999 | Tu et al. |
| 5,999,855 | A | 12/1999 | DiMarco |
| 6,003,517 | A | 12/1999 | Sheffield et al. |
| 6,004,269 | A | 12/1999 | Crowley et al. |
| 6,006,755 | A | 12/1999 | Edwards |
| 6,009,877 | A | 1/2000 | Edwards |
| 6,010,500 | A | 1/2000 | Sherman et al. |
| 6,014,579 | A | 1/2000 | Pomeranz et al. |
| 6,016,437 | A | 1/2000 | Tu et al. |
| 6,023,638 | A | 2/2000 | Swanson |
| 6,024,740 | A | 2/2000 | Lesh et al. |
| 6,029,091 | A | 2/2000 | De La Rama et al. |
| 6,032,673 | A | 3/2000 | Savage et al. |
| 6,033,397 | A | 3/2000 | Laufer et al. |
| 6,033,404 | A | 3/2000 | Melzer et al. |
| 6,036,687 | A | 3/2000 | Laufer et al. |
| 6,036,689 | A | 3/2000 | Tu et al. |
| 6,039,731 | A | 3/2000 | Taylor et al. |
| 6,045,549 | A | 4/2000 | Smethers et al. |
| 6,045,550 | A | 4/2000 | Simpson et al. |
| 6,050,992 | A | 4/2000 | Nichols |
| 6,053,172 | A | 4/2000 | Hovda et al. |
| 6,056,744 | A | 5/2000 | Edwards |
| 6,056,769 | A | 5/2000 | Epstein et al. |
| 6,066,132 | A | 5/2000 | Chen et al. |
| 6,071,279 | A | 6/2000 | Whayne et al. |
| 6,071,280 | A | 6/2000 | Edwards et al. |
| 6,071,281 | A | 6/2000 | Burnside et al. |
| 6,071,282 | A | 6/2000 | Fleischman |
| 6,083,255 | A | 7/2000 | Laufer et al. |
| 6,092,528 | A | 7/2000 | Edwards |
| 6,102,886 | A | 8/2000 | Lundquist et al. |
| 6,119,030 | A | 9/2000 | Morency |
| 6,123,703 | A | 9/2000 | Tu et al. |
| H0001905 | H | 10/2000 | Hill |
| 6,129,751 | A | 10/2000 | Lucchesi et al. |
| 6,139,527 | A | 10/2000 | Laufer et al. |
| 6,142,993 | A | 11/2000 | Whayne et al. |
| 6,143,013 | A | 11/2000 | Samson et al. |
| 6,149,647 | A | 11/2000 | Tu et al. |
| 6,152,899 | A | 11/2000 | Farley et al. |
| 6,159,194 | A | 12/2000 | Eggers et al. |
| 6,179,833 | B1 | 1/2001 | Taylor |
| 6,183,468 | B1 | 2/2001 | Swanson et al. |
| 6,198,970 | B1 | 3/2001 | Freed et al. |
| 6,200,311 | B1 | 3/2001 | Danek et al. |
| 6,200,332 | B1 | 3/2001 | Del Giglio |
| 6,200,333 | B1 | 3/2001 | Laufer |
| 6,210,367 | B1 | 4/2001 | Carr |
| 6,214,002 | B1 | 4/2001 | Fleischman et al. |
| 6,216,043 | B1 | 4/2001 | Swanson et al. |
| 6,216,044 | B1 | 4/2001 | Kordis |
| 6,217,576 | B1 | 4/2001 | Tu et al. |
| 6,231,571 | B1 | 5/2001 | Ellman et al. |
| 6,235,024 | B1 | 5/2001 | Tu |
| 6,241,727 | B1 | 6/2001 | Tu et al. |
| 6,251,104 | B1 | 6/2001 | Kesten et al. |

(56) References Cited

U.S. PATENT DOCUMENTS

| | | |
|---|---|---|
| 6,254,598 B1 | 7/2001 | Edwards et al. |
| 6,258,083 B1 | 7/2001 | Daniel et al. |
| 6,258,087 B1 | 7/2001 | Edwards et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,325,795 B1 | 12/2001 | Lindemann et al. |
| 6,338,727 B1 | 1/2002 | Noda et al. |
| 6,338,836 B1 | 1/2002 | Kuth et al. |
| 6,355,031 B1 | 3/2002 | Edwards et al. |
| 6,379,349 B1 | 4/2002 | Muller et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,423,058 B1 | 7/2002 | Edwards et al. |
| 6,423,105 B1 | 7/2002 | Iijima et al. |
| 6,425,895 B1 | 7/2002 | Swanson et al. |
| 6,428,538 B1 | 8/2002 | Blewett et al. |
| 6,438,400 B1 | 8/2002 | Beard et al. |
| 6,440,129 B1 | 8/2002 | Simpson |
| 6,442,435 B2 | 8/2002 | King et al. |
| 6,460,545 B2 | 10/2002 | Kordis |
| 6,488,673 B1 | 12/2002 | Laufer et al. |
| 6,493,589 B1 | 12/2002 | Medhkour et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,572,612 B2 | 6/2003 | Stewart et al. |
| 6,575,623 B2 | 6/2003 | Werneth |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,613,002 B1 | 9/2003 | Clark et al. |
| 6,620,159 B2 | 9/2003 | Hegde |
| 6,626,903 B2 | 9/2003 | McGuckin, Jr. et al. |
| 6,634,363 B1 | 10/2003 | Danek et al. |
| 6,638,273 B1 | 10/2003 | Farley et al. |
| 6,638,275 B1 | 10/2003 | McGaffigan et al. |
| 6,640,120 B1 | 10/2003 | Swanson et al. |
| 6,645,199 B1 | 11/2003 | Jenkins et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,749,607 B2 | 6/2004 | Edwards et al. |
| 6,767,347 B2 | 7/2004 | Sharkey et al. |
| 6,770,070 B1 * | 8/2004 | Balbierz .................. 606/41 |
| 6,802,843 B2 | 10/2004 | Truckai et al. |
| 6,805,131 B2 | 10/2004 | Kordis |
| 6,827,717 B2 | 12/2004 | Brommersma et al. |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,869,437 B1 | 3/2005 | Hausen et al. |
| 6,872,206 B2 | 3/2005 | Edwards et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,923,806 B2 * | 8/2005 | Hooven et al. .................. 606/41 |
| 6,954,977 B2 | 10/2005 | Maguire et al. |
| 7,001,382 B2 | 2/2006 | Gallo, Sr. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,118,568 B2 | 10/2006 | Hassett et al. |
| 7,122,033 B2 | 10/2006 | Wood |
| 7,186,251 B2 | 3/2007 | Malecki et al. |
| 7,198,635 B2 | 4/2007 | Danaek et al. |
| 7,200,445 B1 | 4/2007 | Dalbec et al. |
| 7,211,041 B2 | 5/2007 | Mueller |
| 7,335,197 B2 * | 2/2008 | Sage et al. .................. 606/41 |
| 7,425,212 B1 | 9/2008 | Danek et al. |
| 7,507,232 B1 | 3/2009 | Garito et al. |
| 7,556,624 B2 | 7/2009 | Laufer et al. |
| 8,409,194 B1 * | 4/2013 | Ellman .................. 606/41 |
| 8,814,856 B2 * | 8/2014 | Elmouelhi et al. ........... 606/41 |
| 2002/0022870 A1 * | 2/2002 | Truckai ............. A61B 18/1485 |
| | | 607/101 |
| 2002/0072737 A1 | 6/2002 | Belden et al. |
| 2002/0123748 A1 | 9/2002 | Edwards et al. |
| 2002/0147391 A1 | 10/2002 | Morency |
| 2002/0173785 A1 | 11/2002 | Spear et al. |
| 2003/0050631 A1 | 3/2003 | Mody et al. |
| 2003/0065371 A1 | 4/2003 | Satake |
| 2003/0109778 A1 | 6/2003 | Rashidi |
| 2003/0149395 A1 * | 8/2003 | Zawacki .................. 604/40 |
| 2003/0159700 A1 | 8/2003 | Laufer et al. |
| 2003/0233099 A1 | 12/2003 | Danaek et al. |
| 2004/0024410 A1 * | 2/2004 | Olson et al. .................. 606/93 |
| 2004/0031494 A1 | 2/2004 | Danek et al. |
| 2004/0153056 A1 | 8/2004 | Muller et al. |
| 2004/0182399 A1 | 9/2004 | Danek et al. |
| 2004/0193243 A1 | 9/2004 | Mangiardi et al. |
| 2004/0249401 A1 | 12/2004 | Rabiner et al. |
| 2005/0010138 A1 | 1/2005 | Mangiardi et al. |
| 2005/0010270 A1 | 1/2005 | Laufer |
| 2005/0049586 A1 | 3/2005 | Daniel et al. |
| 2005/0061771 A1 * | 3/2005 | Murphy .................. 216/17 |
| 2005/0085880 A1 * | 4/2005 | Truckai ............. A61B 18/1485 |
| | | 607/101 |
| 2005/0096644 A1 | 5/2005 | Hall et al. |
| 2005/0154386 A1 * | 7/2005 | West et al. .................. 606/41 |
| 2005/0182431 A1 | 8/2005 | Hausen et al. |
| 2005/0203503 A1 | 9/2005 | Edwards et al. |
| 2005/0240176 A1 | 10/2005 | Oral et al. |
| 2005/0272971 A1 | 12/2005 | Ohnishi et al. |
| 2005/0288664 A1 * | 12/2005 | Ford et al. .................. 606/41 |
| 2006/0062808 A1 | 3/2006 | Laufer et al. |
| 2006/0089637 A1 | 4/2006 | Werneth et al. |
| 2006/0100652 A1 * | 5/2006 | Beaupre .................. 606/169 |
| 2006/0135953 A1 | 6/2006 | Kania et al. |
| 2006/0212032 A1 | 9/2006 | Daniel et al. |
| 2006/0247617 A1 | 11/2006 | Danek et al. |
| 2006/0247618 A1 * | 11/2006 | Kaplan et al. .................. 606/41 |
| 2006/0247619 A1 | 11/2006 | Kaplan et al. |
| 2006/0247746 A1 | 11/2006 | Danek et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0265035 A1 | 11/2006 | Yachi et al. |
| 2006/0282071 A1 | 12/2006 | Utley et al. |
| 2007/0021745 A1 | 1/2007 | McIntyre et al. |
| 2007/0055228 A1 | 3/2007 | Berg et al. |
| 2007/0093802 A1 | 4/2007 | Danek et al. |
| 2007/0100390 A1 | 5/2007 | Danaek |
| 2007/0106292 A1 | 5/2007 | Kaplan et al. |
| 2007/0106296 A1 | 5/2007 | Laufer et al. |
| 2007/0118184 A1 | 5/2007 | Danek et al. |
| 2007/0123958 A1 | 5/2007 | Laufer |
| 2007/0123961 A1 | 5/2007 | Danek et al. |

(56) References Cited

U.S. PATENT DOCUMENTS

| | | |
|---|---|---|
| 2007/0208336 A1 | 9/2007 | Kim et al. |
| 2008/0103498 A1 | 5/2008 | West et al. |
| 2008/0172048 A1 | 7/2008 | Martin et al. |
| 2008/0312649 A1 | 12/2008 | Guerra et al. |
| 2008/0312650 A1 | 12/2008 | Daniel et al. |
| 2008/0319436 A1 | 12/2008 | Daniel et al. |
| 2009/0018538 A1 | 1/2009 | Webster et al. |
| 2009/0043301 A1 | 2/2009 | Jarrard et al. |
| 2009/0043302 A1 | 2/2009 | Ford et al. |
| 2009/0069797 A1 | 3/2009 | Danek et al. |
| 2009/0275864 A1 | 11/2009 | Hirai |
| 2010/0023006 A1* | 1/2010 | Ellman ............... 606/45 |
| 2010/0042096 A1 | 2/2010 | Ellman |
| 2010/0094288 A1 | 4/2010 | Kerr |
| 2010/0160906 A1 | 6/2010 | Jarrard |
| 2010/0193569 A1 | 8/2010 | Yates et al. |
| 2010/0292684 A1 | 11/2010 | Cybulski et al. |
| 2011/0028963 A1 | 2/2011 | Gilbert |
| 2011/0071518 A1 | 3/2011 | Gilbert |
| 2011/0087213 A1 | 4/2011 | Messerly et al. |
| 2014/0350553 A1* | 11/2014 | Okuyama ............ 606/41 |

FOREIGN PATENT DOCUMENTS

| | | |
|---|---|---|
| EP | 0 873 710 A2 | 10/1998 |
| EP | 908713 A1 | 4/1999 |
| EP | 908150 B1 | 5/2003 |
| EP | 1297795 B1 | 8/2005 |
| EP | 2 170 459 B1 | 2/2014 |
| FR | 2659240 B1 | 7/1997 |
| JP | 7289557 A2 | 11/1995 |
| RU | 2053814 C1 | 2/1996 |
| RU | 2091054 C1 | 9/1997 |
| WO | WO-8911311 A1 | 11/1989 |
| WO | WO-9304734 A1 | 3/1993 |
| WO | WO-9502370 A3 | 1/1995 |
| WO | WO-951 0322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO 98/46150 A1 | 10/1998 |
| WO | WO-9844854 A1 | 10/1998 |
| WO | WO-9852480A 1 | 11/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9934741 A1 | 7/1999 |
| WO | WO-9944506 A1 | 9/1999 |
| WO | WO-9945855 A1 | 9/1999 |
| WO | WO-0051510 A1 | 9/2000 |
| WO | WO 00/62699 A2 | 10/2000 |
| WO | WO-0103642 A1 | 1/2001 |
| WO | WO 02/32334 A1 | 4/2002 |
| WO | WO 2006/007284 A2 | 1/2006 |
| WO | WO 2006/044581 A2 | 4/2006 |
| WO | WO 2008/051706 A2 | 5/2008 |

OTHER PUBLICATIONS

Co-pending U.S. Appl. No. 09/095,323, filed Jun. 10, 1998.
Co-pending U.S. Appl. No. 09/244,173, filed Feb. 4, 1999.
U.S. Appl. No. 60/951,655, filed Jul. 24, 2007.
Co-pending U.S. Appl. No. 12/640,644, filed Dec. 17, 2009, Inventor Jerry Jarrard.
PCT International Search Report for application No. PCT/US08/65867 dated Oct. 1, 2008, 1 page.
Co-pending U.S. Appl. No. 11/551,639.
Co-pending U.S. Appl. No. 09/095,323.
Co-pending U.S. Appl. No. 09/244,173.
U.S. Appl. No. 60/951,655.
Dierkesmann et al. Indication and Results of Endobronchial Laser Therapy, Lung, 1990, 168, 1095-1102.
Ivanyuta O. M. et al. Effect of Low-Power Laser Irradiation of Bronchial Mucosa on the State of Systemic and Local Immunity in Patients with Chronic Bronchitis, Problemy Tuberkuleza, 1991, 6, 26-29.
James C. Hogg, The Pathology of Asthma, APMIS, Oct. 1997, 105(10), 735-745.
Macklem P.T., Mechanical Factors Determining Maximum Bronchoconstriction, European Respiratory Journal, Jun. 1989, 6, 516s-519s.
Netter, F.H, Respiratory System: A Compilation of Paintings Depicting Anatomy and Embryology, Physiology, Pathology, Pathophysiology, and Clinical Features and Treatment of Diseases ,In The CIBA Collection of Medical Illustrations M.B. Divertie, ed., Summit: New Jersey, 1979, vol. 7, 119-135.
Provotorov et al. The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 62 (12),18-23.
Simon R. Johnson, et al. Synthetic Functions of Airway Smooth Muscle in Asthma, Trends Pharmacol. Sci., Aug. 1997, 18(8), 288-292.
Vorotnev et al. Low energy laser treatment of chronic obstructive bronchitis in a general rehabilitation center ,ISSN: 0040-3660., Terapevticheskii Arkhiv, 1997, 69 (3), 17-19.
Wiggs B.R. et al. On the Mechanism of Mucosal Folding in Normal and Asthmatic Airways, J. Appl. Physiol., Dec. 1997, 83(6), 1814-1821.

* cited by examiner

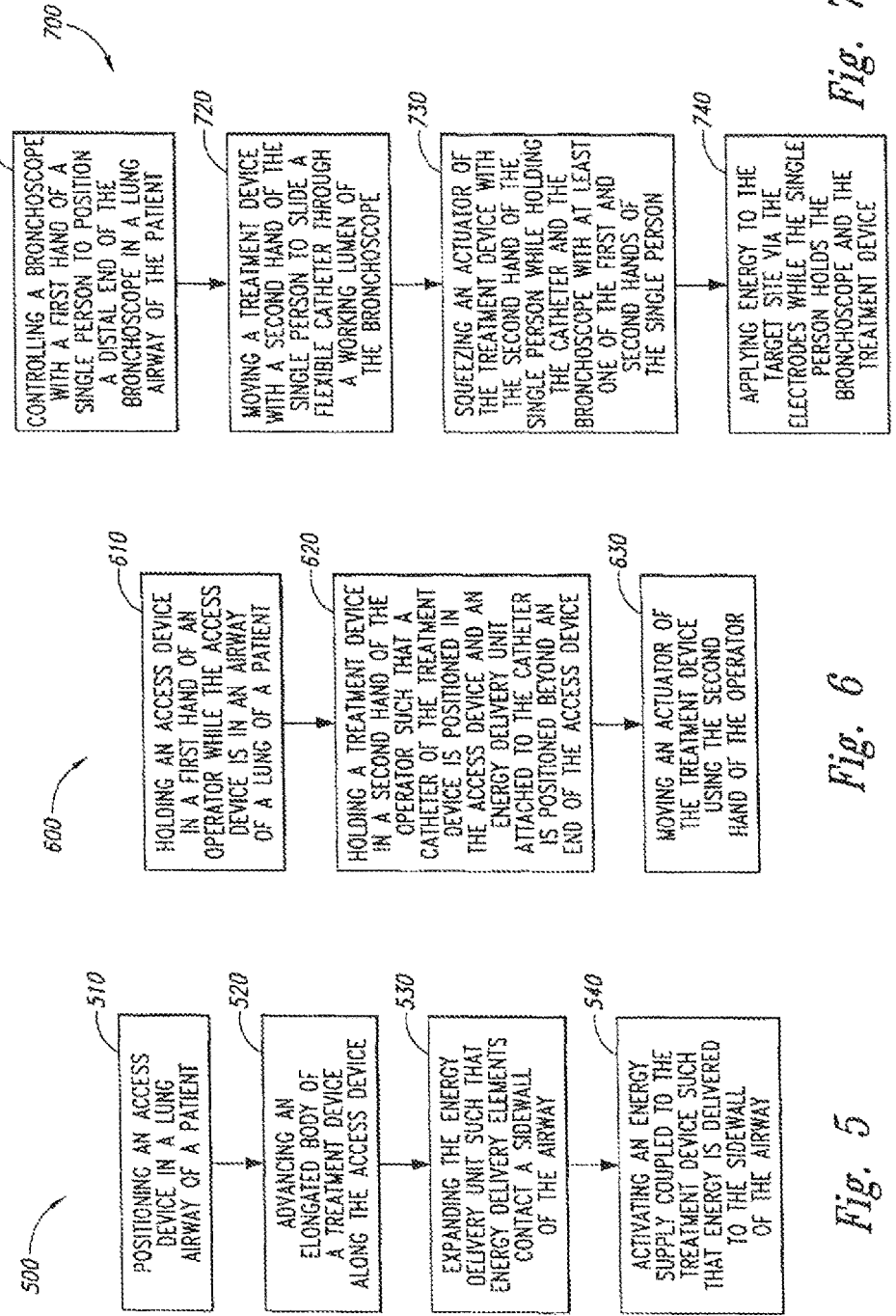

SYSTEMS AND METHODS FOR DELIVERING ENERGY TO PASSAGEWAYS IN A PATIENT

This application is a continuation of U.S. patent application Ser. No. 11/777,225, filed on Jul. 12, 2007 (now U.S. Pat. No. 8,235,983), the contents of which are incorporated by reference in their entirety.

TECHNICAL FIELD

The present invention is directed to medical systems and methods for delivering energy to passageways in a patient, such as airways in the lung of a patient to reduce the resistance to airflow.

BACKGROUND

Asthma is a disease that makes it difficult to breathe and in many cases can be debilitating. Asthma is generally manifested by (i) bronchoconstriction, (ii) excessive mucus production, and/or (iii) inflammation and swelling of airways that cause widespread but variable airflow obstructions. Asthma can be a chronic disorder often characterized by persistent airway inflammation, but asthma can be further characterized by acute episodes of additional airway narrowing via contraction of hyper-responsive airway smooth muscle tissue.

Conventional pharmacological approaches for managing asthma include: (i) administering anti-inflammatories and long-acting bronchodilators for long-term control, and/or (ii) administering short-acting bronchodilators for management of acute episodes. Both of these pharmacological approaches generally require repeated use of the prescribed drugs at regular intervals throughout long periods of time. However, high doses of corticosteroid anti-inflammatory drugs can have serious side effects that require careful management, and some patients are resistant to steroid treatment even at high doses. As such, effective patient compliance with pharmacologic management and avoiding stimulus that triggers asthma are common barriers to successfully managing asthma.

Asthmatx, Inc. has developed new asthma treatments that involve applying energy to alter properties of the smooth muscle tissue or other tissue (e.g., nerves, mucus glands, epithelium, blood vessels, etc.) of airways in a lung of a patient. Several embodiments of methods and apparatus related to such treatments are disclosed in commonly-assigned U.S. Pat. Nos. 6,411,852, 6,634,363, and 7,027,869; and U.S. Published Application No. US2005/0010270, all of which are incorporated by reference herein in their entirety.

Many embodiments of the foregoing asthma treatments that apply energy to tissue of the airways use catheters that can be passed (e.g., navigated) through the tortuous pathways defined by the lung airways. FIG. 1, for example, illustrates a bronchial tree 90 in which the various bronchioles 92 decrease in size and have many branches 96 as they extend from the right and left bronchi 94. Accordingly, the treatment devices should be configured to treat airways of varying sizes as well as function properly when repeatedly deployed after navigating through the tortuous anatomy.

In a typical application, a first medical practitioner (e.g., a bronchoscopist) navigates a distal portion of a bronchoscope through the tortuous pathways of the lung until the distal tip of the bronchoscope is at a desired region of an airway. A second medical practitioner (e.g., a nurse or medical assistant) in addition to the first practitioner assists in advancing a catheter of a treatment device through a working lumen of the bronchoscope until a distal portion of the catheter projects out from the distal end of the bronchoscope. After positioning the distal portion of the catheter at a desired first airway site, the first or second practitioner uses one hand to hold the catheter in place relative to the bronchoscope while the second practitioner moves the thumb of one or the other free hand to move a slide-type actuator in a distal) direction to drive an electrode array distally out of the catheter. The second practitioner continues to move the slide-type actuator in the distal direction to drive a plurality of electrodes outwardly until the electrodes contact the sidewall of the airway at a first contact site. The first or second medical practitioner then operates a switch that activates an energy source to deliver energy to the first contact site for a treatment period.

After terminating the energy delivery, (i) the second practitioner slides the actuator in a proximal direction to contract the electrodes, (ii) the first or second practitioner repositions the catheter axially along the bronchoscope and the airway to a second contact site, and (iii) with the catheter held in place, the second practitioner slides the actuator distally to re-expand the electrodes until they contact the sidewall of the airway at the second contact site. The first or second practitioner then activates the energy supply to deliver energy to the second contact site for another treatment period. This process is repeated several times at 3-30 mm increments throughout several regions of the variable sized airways in a lung of a patient. As such, this process requires good coordination and communication between the first and second practitioners to treat a patient, but even then such communication takes time. A typical treatment protocol for treating the full lung of a patient can accordingly require three 30-60 minute sessions, which often results in practitioner fatigue.

The tortuous configuration of the lung airways also presents other challenges to efficiently delivering energy to the airway tissue. For example, the treatment device should be sufficiently flexible to follow the working lumen of a bronchoscope and help facilitate accurate steering of the bronchoscope, and the treatment device should enable accurate, reliable deployment of the electrodes at the distal end of the catheter. Friction losses along the catheter, however, can restrict expansion/contraction of the electrodes because only a portion of the force from the actuator is transmitted to the electrode array. This can inhibit the electrodes from appropriately (e.g., fully) contacting the sidewall of the airway, which may reduce the efficacy of the treatment. Additionally, friction along the catheter increases the load on the thumb of the second practitioner as the slide-type actuator is repeatedly moved, which may cause fatigue and also may make it difficult to sense when the electrodes engage the variable sized airways.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the disclosure and are not intended to limit the scope of the disclosure.

FIG. 5 is a flow chart of a method for treating tissue in an internal passageway of a patient in accordance with an embodiment of the disclosure.

FIG. 6 is a flow chart of a method of treating an internal airway in a lung of a patient in accordance with an embodiment of the disclosure.

FIG. 7 is a flow chart of a method of treating an internal airway in a lung of a patient in accordance with another embodiment of the disclosure.

DETAILED DESCRIPTION

Specific details of several embodiments of the disclosure are described below with reference to systems and methods for delivering energy to passageways in a patient. Although many of the embodiments are described below with respect to delivering radio frequency energy to airways in a lung of a patient to treat asthma, other embodiments that deliver other energy modalities to lung airways or other types of passageways for treating other indications may be within the scope of the invention. For example, other types of energy modalities can include thermal (resistive and/or infrared), microwave, laser, ultrasonic (e.g., HIFU), cryo-ablation, radiation, and/or other energy modalities. Moreover, several other embodiments of the invention can have different configurations, components, or procedures than those described in this section. A person of ordinary skill in the art, therefore, will accordingly understand that the invention may have other embodiments with additional elements, or the invention may have other embodiments without several of the features shown and described below with reference to FIGS. 2A-8B. It will further be appreciated that the above depictions are for illustrative purposes only and do not necessarily reflect the actual shape, size, or dimensions of the system or device.

Figure 1:
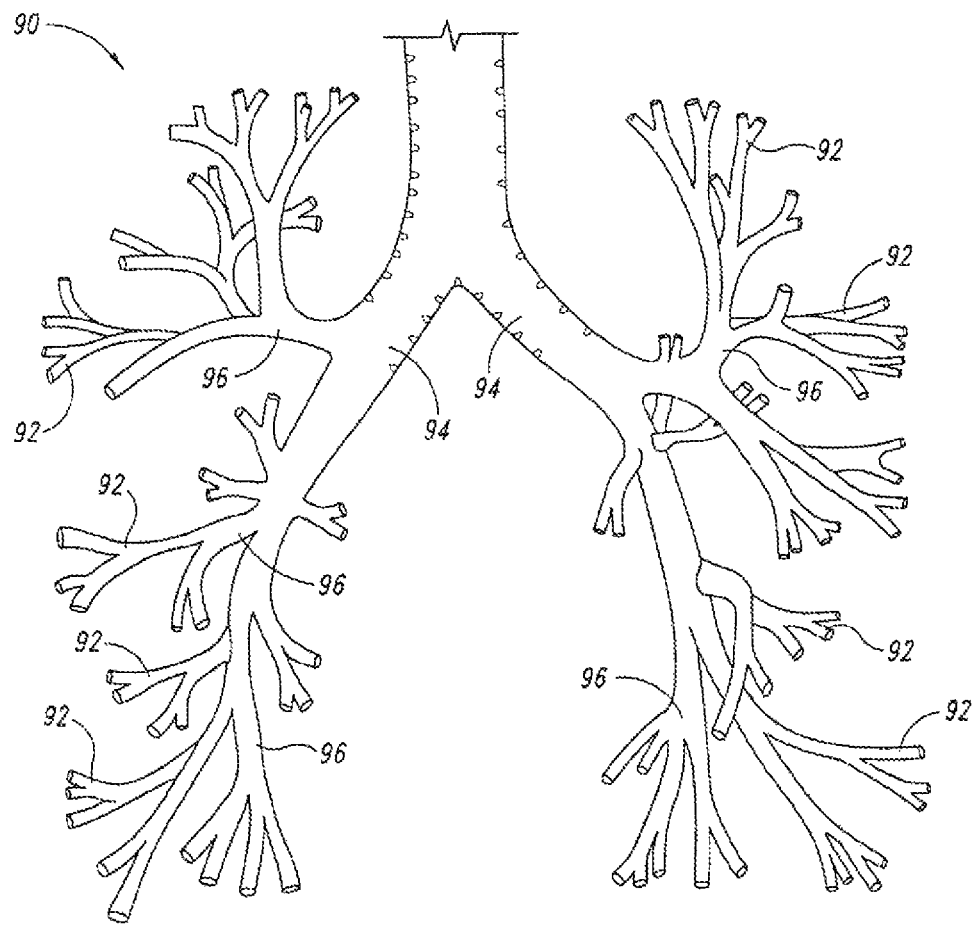
FIG. 1 illustrates representative airways in a lung of a human patient.
Figure 2A:
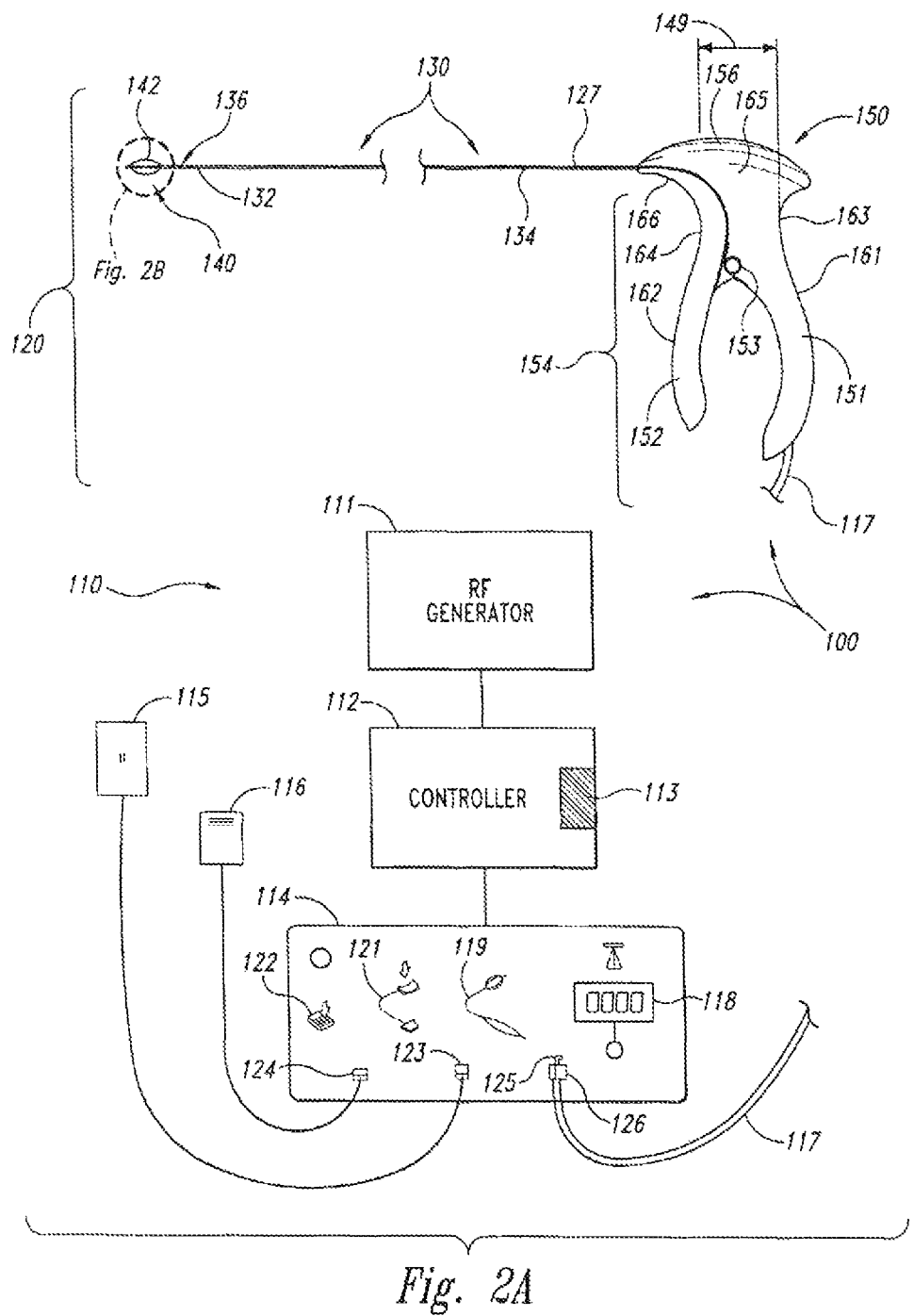
FIG. 2A is a schematic view illustrating a system for delivering energy to passageways in a patient in accordance with an embodiment of the disclosure.

FIG. 2A is a schematic view illustrating a system 100 for delivering energy to passageways in a patient having a power/control unit 110 and an energy delivery device 120 in accordance with an embodiment of the disclosure. The power/control unit 110 can include an energy generator 111 (e.g., power supply), a controller 112 having a processor 113, and a user interface 114. The energy generator 111 and controller 112 can provide radio frequency (RF) energy to the energy delivery device 120, but other embodiments of the energy generator 111 and controller 112 can provide other energy modalities. The controller 112 can contain safety algorithms and other control algorithms that control (i) the power output to the energy delivery device 120 and (ii) the indicators 118, 119, 121, 122 of the user interface 114. The power/control unit 110 can further include one or more connections 123, 124, 125 for an optional return electrode 115 for monopolar RF configurations, an optional switch 116 (e.g., an actuation pedal) for directing the controller 112 to cause the energy generator 111 to provide energy, and a conductive line 117 and connector 126 coupled to the energy delivery device 120.

Suitable embodiments of the power/control unit are disclosed in U.S. Pat. No. 7,104,987 and U.S. Published Application No. US2006/0247746, the entireties of which are incorporated by reference herein. The system may deliver energy to target sites via the treatment device 100 in a variety of treatment patterns. Further details with respect to energy modalities and/or examples of treatment patterns may be found in commonly-assigned U.S. Pat. No. 6,411,852.

The energy delivery device 120 is an example of a treatment device for treating asthma or other indications associated with passageways in a human. The embodiment of the energy delivery device 120 illustrated in FIG. 2A includes an elongated body 130 with a distal portion 132 and a proximal portion 134, an energy delivery unit 140 at the distal portion 132, and a handle 150 at the proximal portion 134. The length of the elongated body 130 should be sufficient to access the target tissue in airways of the lung or other passageways targeted for treatment. For example, the length of the elongated body 130 can be from approximately 0.5-8 feet to allow passage though a bronchoscope and reach targeted airways deep within the lungs. The elongated body 130 can also be configured to treat airways as small as 3 mm in diameter, but the elongated body 130 is not limited to treating airways of any particular size such that airways smaller or larger than 3 mm may be treated. Typically, the delivery unit 140 expands/contracts to variable sizes to treat airways between 3-10 mm.

Several embodiments of the elongated body 130 are flexible catheters configured to slide through the working lumen of an access device (e.g., bronchoscope). The elongated body 130 can also include a plurality of markers 136 at the distal section 132 to position the energy delivery unit 140 relative to an access device (not shown in FIG. 2A) and a proximal marker(s) 127 so as to assist in expedient positioning of the energy delivery unit 140 out of the distal end of the access device. Specific embodiments of elongated bodies with markers suitable for use in the system 100 are described below with reference to FIGS. 8A and 8B, and in U.S. patent application Ser. No. 11/551,639 and in U.S. Published Application No. US2007/0106292, which are incorporated herein by reference in their entirety.

Figure 2B:
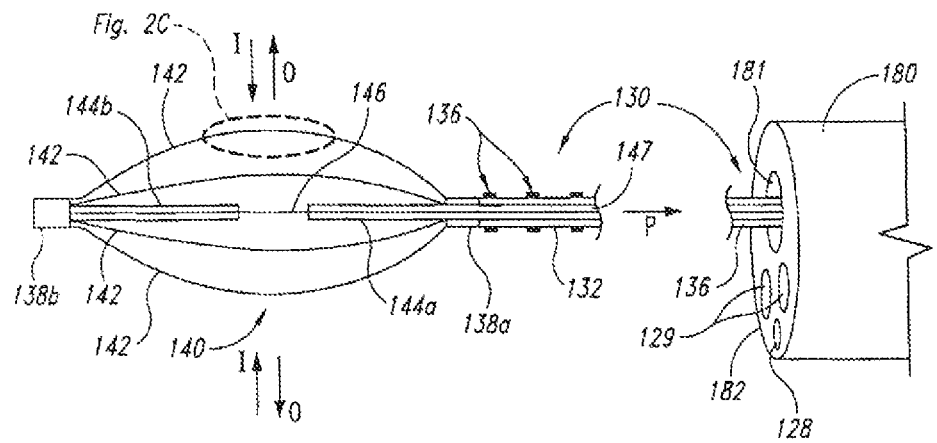
FIG. 2B is a side view in partial cross-section of a portion of an energy delivery device for use with the system of FIG. 2A in accordance with an embodiment of the disclosure.

The energy delivery unit 140 can have at least one energy delivery element, such as an electrode 142, configured to deliver energy to the tissue of an airway or other passageway in the patient. FIG. 2B is a partial cross-sectional view showing an embodiment of the energy delivery unit 140 in greater detail. In this embodiment, the energy delivery unit 140 includes four electrodes 142, a proximal sleeve 138a and a proximal alignment extrusion or retainer 144a fixed to the elongated body 130 and attached to the proximal ends of the electrodes 142, and a distal sleeve 138b and a distal alignment extrusion or retainer 144b attached to the distal ends of the electrodes 142. The energy delivery device 120 can also include a wire 146 attached to the distal retainer 144b at the distal sleeve 138b and configured to move through a lumen 147 of the elongated body 130 and the proximal retainer 144a.

The example of the energy delivery unit 140 illustrated in FIG. 2B is a "basket-type" configuration in which the electrodes 142 move outwardly (arrows O) as the wire 146 moves proximally (arrow P) relative to the elongated body 130. The electrodes 142 can move inwardly (arrows I) by releasing the wire 146 such that a spring or other resilient element in the handle 150, and/or the spring force of the electrodes 142, drives the wire 146 distally. The outward/inward movement of the electrodes 142 is useful when the device is operated intraluminally or in airways in the lungs because the energy delivery unit 140 can be advanced through a working lumen 181 of an access device 180 while the electrodes 142 are in a low-profile configuration, and then the electrodes 142 can repeatedly be moved outwardly according to the varying sizes of the passageways. In this illustration, the pull wire 146 may also comprise a conductive wire between the electrodes 142 and the energy supply 111. Specific embodiments of suitable electrodes and retainers for preventing electrode inversions and limiting basket expansions are disclosed in U.S. Publication No. US2007/0106292.

Figure 2C:
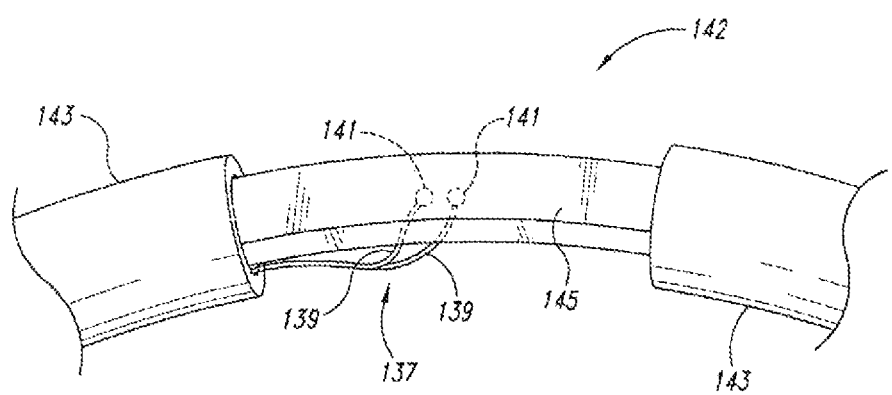
FIG. 2C is an exploded view of a portion of an electrode of the energy delivery device of FIG. 2B in accordance with an embodiment of the disclosure.

FIG. 2C is an exploded view illustrating a portion of one electrode 142 in greater detail. The electrode 142 has an outer insulating material or coating 143 at proximal and distal ends so as to define a non-insulated, active central portion 145 of the electrode 142 which delivers controlled energy to the tissue walls. A thermocouple 137 having thermocouple leads 139 is attached and in electrical communication to the active portion 145 of the electrode 142 at separate joints 141. The circuit may be triggered (e.g., open circuit) if either joint becomes detached so that the thermocouple 137 stops reading temperature. Specific embodiments of suitable electrode and thermocouple configurations are disclosed in U.S. Publication No. US2007/0118184, which is incorporated herein by reference in its entirety.

Referring back to FIG. 2A, the illustrated example of the handle 150 is configured so that a single operator can hold an access device (e.g., a bronchoscope) in one hand (e.g., a first hand) and use the other hand (e.g., a second hand) to (i) advance the elongated body 130 through a working lumen of the access device until the energy delivery unit 140 projects beyond the distal end of the access device and is positioned at a desired target site, and (ii) pull the wire 146 (FIG. 2B) to move the electrodes 142 outwardly until they contact the sidewall of an airway passage while the catheter is held in place relative to the access device with a single hand (e.g., the same second hand). The same operator can also operate the switch 116 of the power/control unit 110 such that the entire procedure can be performed by a single person.

In one embodiment, the handle 150 has a first portion 151 and a second portion 152 rotatably coupled to the first portion 151 by a joint 153. The first portion 151 and/or the second portion 152 are one example of an actuator for manipulating the electrodes 142. The first and second portions 151-152 can be configured to form a grip 154 and a head 156 located at an upper portion of the grip 154. The head 156, for example, can project outwardly from the grip such that a portion of the grip 154 is narrower than the head 156. In the specific embodiment illustrated in FIG. 2A, the first portion 151 has a first curved surface 161 with a first neck portion 163 and a first collar portion 165, and the second portion 152 has a second curved surface 162 with a second neck portion 164 and a second collar portion 166. The first and second curved surfaces 161-162 can be configured such that they are arranged to define a hyperbolic-like shaped grip when viewed from a side elevation.

The portion of the handle 150 at the first and second neck portions 163-164 provides a neck around which the thumb and forefinger of an operator can extend, and the first and second collar portions 165-166 are configured to be supported by the thumb and forefinger of the operator. The handle 150 can also include a torsion spring (not shown) at the joint 153, or another suitable resilient element, to drive the lower ends of the first and second portions 151-152 apart from each other. In addition, the spring torsion may be selected to provide a difference in sensation between handle actuation in air as opposed to a counter force of the airway wall (e.g., a less robust spring). In operation, a single user moves the lower ends of the first and second portions 151-152 together (arrow R in FIG. 3A) while simultaneously controlling the position of the elongated body 130 in the airway of the patient with a single hand as explained in more detail below. After applying energy to the tissue for a treatment period, the operator relaxes his/her grip and the torsion spring drives the lower ends of the first and second portions 151-152 apart from each other.

Figure 3A:
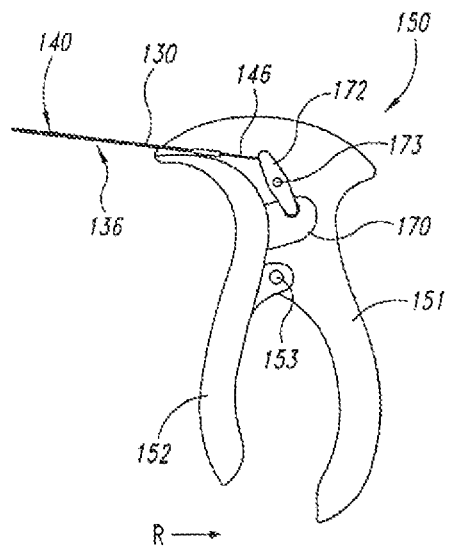
FIGS. 3A and 3B are cross-sectional views and FIG. 3C is a back view of a handle for use with an energy delivery device in accordance with an embodiment of the disclosure.
Figure 3B:
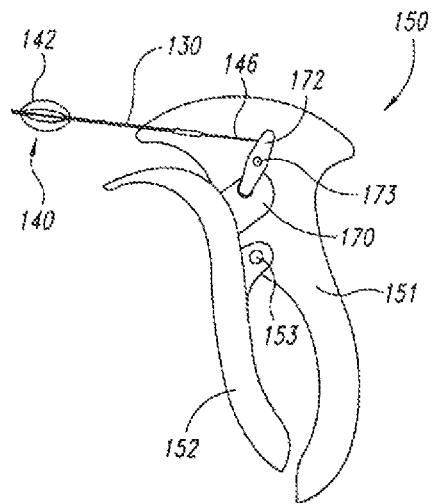

FIGS. 3A and 3B are cross-sectional views illustrating further details of an embodiment of the handle 150 with a section of the first portion 151 removed. In this embodiment, the handle 150 further includes a flange 170 fixed to the second portion 152 and a lever 172 pivotally attached to the first portion 151 by a pin 173. One end of the lever 172 is in a notch in the flange 170, and an opposing end of the lever 172 is attached to the wire 146 that extends through the lumens of the elongated body 130 to the distal retainer 144b (FIG. 2B) of the energy delivery unit 140. The first portion 151 can also include a track element (not shown) that secures the line 117 (FIG. 2A) to the handle 150 via a press fit or zigzag path.

Figure 3C:
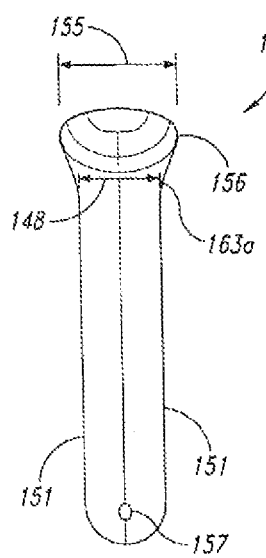

FIG. 3C is a back view illustrating further details of an embodiment of the handle 150. As described above, dimensions of the gripping necks 163-164 are provided such that the gripping neck 154 volume frees up two or three fingers (e.g., thumb and forefinger) of the single operator's hand to manipulate (e.g., advance, repeatedly position, hold in place relative to the bronchoscope seal) the elongated body 130 at the desired target sites within passageways of the patient. The first and second neck portions 163-164 may have a combined width (denoted by arrows 149 in FIG. 2A) in a range from about 0.95 inches to about 1.3 inches. The first (or second) neck portion depth 163a (denoted by arrows 148) may be in a range from about 0.75 inches to about 1.0 inch. The grip portions are narrower than the head 156, which is dimensioned (denoted by arrows 155) in a range from about 1.3 inches to about 1.75 inches, so as to allow the head 156 to be easily cradled by the operator's thumb and forefinger. In this view, an opening 157 in the first portion 151 can be seen for connection of the handle 150 to the conductive line 117.

FIGS. 2B-3C also illustrate an example of operating the system 100. Referring to FIGS. 2B and 3A together, the handle 150 shown in FIG. 3A is in a first position in which the electrodes 142 are in a low-profile configuration. In this configuration, an operator advances the energy delivery unit 140 and the elongated body 130 through the working lumen 181 of the access device 180 until the energy delivery unit 140 projects beyond a distal end 182 of the access device 180. Visualization of this may be facilitated by an imaging lumen 128 and/or light optical fiber lumens 129 of the access device 180 (or optical chip(s) or fiber(s)) mounted at the distal end of the access device). As described in U.S. Published Application No. 2007/0106292, the operator can control the position of the energy delivery unit 140 relative to the access device 180 using the markers 136 on the elongated body 130.

Referring to FIGS. 2B and 3B, the operator squeezes the handle 150 (arrow R) to move the second portion 152 about the joint 153, which causes the flange 170 to rotate the lever 172 in a manner that pulls the wire 146 proximally. The proximal movement of the wire 146 pulls the distal retainer 144b proximally and accordingly moves the electrodes 142 outwardly (arrows O in FIG. 2B). The operator can control the elongated body 130 and rotate the second portion 152 relative to the first portion 151 with a single hand while simultaneously holding the access device 180 in the other hand and/or the same hand. The operator then actuates the switch 116 (FIG. 2A) that activates the energy generator 111 (FIG. 2A) to deliver energy via the electrodes 142 to the tissue of the airway until the controller 112 (FIG. 2A) or the operator deactivates the energy generator. The operator then releases the second portion 152 of the handle to release the tension on the wire 146 so that the electrodes 142 move inwardly (arrows I). The operator can then move the elongated body 130 axially while holding the access device 180 to reposition the energy delivery unit by an increment indicated by the markers 136 and repeat the procedure at another site of the airway.

Figure 4:
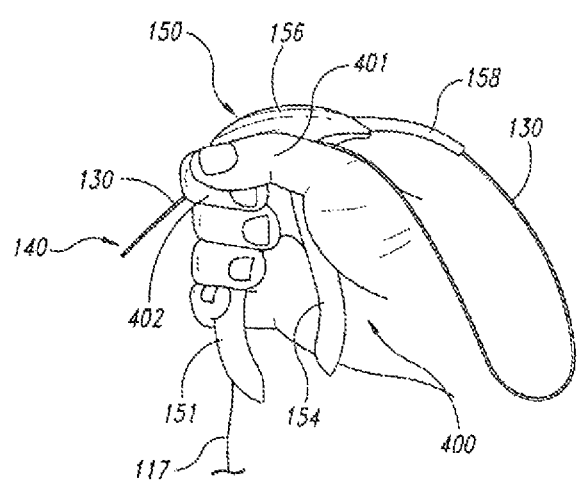
FIG. 4 is an isometric view illustrating an implementation of the handle illustrated in FIGS. 3A and 3B in accordance with an embodiment of the disclosure.

FIG. 4 is an isometric view illustrating an embodiment of how an operator can hold and control both the elongated body 130 and the handle 150 with a single hand to concurrently move the electrodes 142 outwardly and/or inwardly. More specifically, the hand 400 of the operator can hold the grip 154 such that the thumb 401 and the forefinger 402 (i.e., first finger) extend around the neck portion of the grip 154. The outward projection of the head 156 of the handle 150 can be configured to rest on a portion of the thumb 401 and forefinger 402 to further control the handle 150. Further, a reinforcing sheath 158 along the elongated body 130 combined with the reversible handle 150 may direct the most proximal portion 134 away from the hand 400 of the operator so as to enhance single hand control at the bronchoscope seal and single operator control of both the treatment and access devices. In this application, the operator can concurrently grip the elongated body 130 with the distal phalanxes of the thumb 401 and forefinger 402 in a manner that enables the operator to hold the elongated body 130 at a precise location. The operator can also squeeze/release the handle 150 with at least one of a second-fourth (e.g., second, third, or fourth) finger of the hand 400 to move the electrodes outwardly/inwardly.

FIG. 5 is a flow chart illustrating a method 500 for treating tissue in an internal passageway of a patient in accordance with one embodiment. The method 500 includes positioning an access device in a lung airway of a patient (block 510). The method 500 further includes advancing an elongated body of a treatment device, such as an embodiment of the energy delivery devices described above, along the access device (block 520). The elongated body is advanced along the access device until an energy delivery unit at a distal portion of the elongated body projects from the access device and is positioned at a desired treatment site. The method 500 further includes expanding the energy delivery unit such that electrodes or other energy delivery elements contact a sidewall of the airway while the elongated body is held in place (block 530), and activating an energy supply coupled to the treatment device such that energy is delivered to the sidewall of the airway (block 540). The method 500 is conducted by a single person such that the single person physically operates both the access device and the treatment device while expanding the energy delivery unit and activating the energy supply.

FIG. 6 is a flow chart illustrating a method 600 for treating an internal airway in a lung of a patient using an embodiment of the system 100. The method 600 includes holding an access device in a first hand of an operator while the access device is in an airway of a lung of a patient (block 610). The method 600 further includes holding a treatment device in a second hand of the operator such that (i) a catheter of the treatment device is positioned in the access device (block 620) and (ii) an energy delivery unit attached to the catheter is positioned beyond an end of the access device. The method 600 also includes moving an actuator of the treatment device while holding the energy delivery unit in place using the second hand of the operator (block 630) such that at least a portion of the energy delivery unit contacts a sidewall of the airway and delivers energy to the airway while the operator's first hand holds the access device.

FIG. 7 is a flow chart of a method 700 for treating an internal airway in a lung of a patient in accordance with another embodiment. The method 700 includes controlling a bronchoscope with a first hand of a single operator to position a distal end of a bronchoscope in a lung airway of the patient (block 710). The method 700 further includes moving a treatment device with a second hand of the single person to slide a flexible catheter through a working lumen of the bronchoscope (block 720). The single person, for example, moves the treatment device until the electrode assembly of the treatment device projects beyond the distal end of the bronchoscope at a first treatment site in the lung airway. The method 700 further includes squeezing an actuator of the treatment device with a second hand of the single person while holding the catheter and the bronchoscope with at least one of the first and second hands of the single person (block 730). The actuator causes electrodes of the electrode assembly to move outwardly to contact the airway. The method 700 can further include applying energy to the target site via the electrodes while the single person holds the bronchoscope and the treatment device (block 740).

Several embodiments of the system 100 provide an ergonomic and efficient treatment device. The handle 150, for example, reduces thumb-fatigue associated with other devices because the handle 150 is actuated with a squeezing motion using larger muscles instead of a sliding motion using primarily muscles associated with the thumb. The system 100 can also be operated by a single person such that it eliminates delays that can occur in systems that require both a first practitioner and a second practitioner to operate the access device and the treatment device. Several embodiments of the system 100 may accordingly treat more patients in a fixed time period, treat patients with reduced treatment time or sessions, and/or treat more passageways within a patient in a single session. Further, a single operator procedure ensures greater accuracy of treatment device placements, and hence treatment patterns.

Figure 8A:
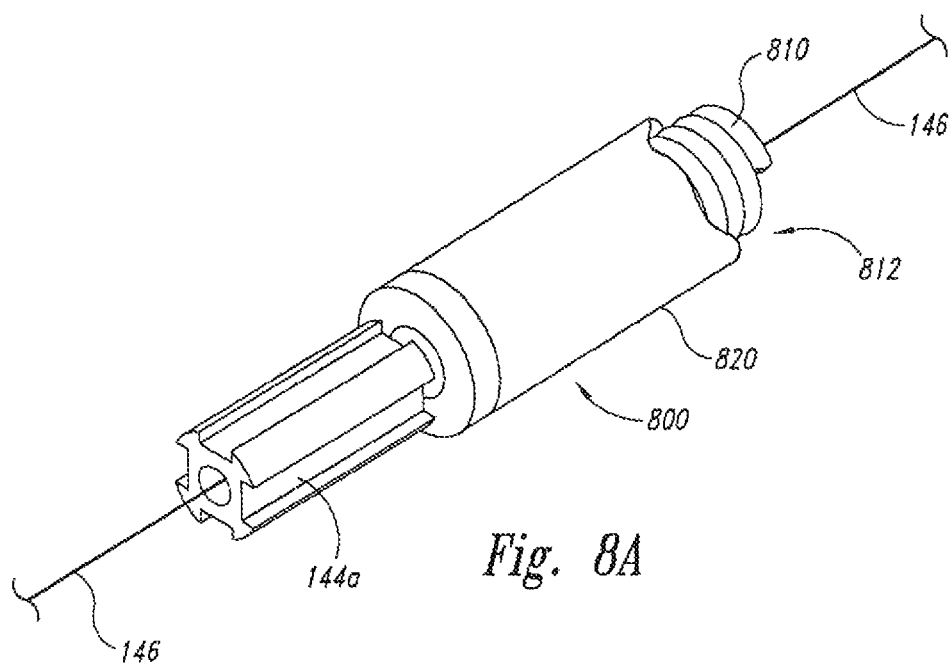
FIG. 8A is an isometric view with a cutaway portion and FIG. 8B is a cross-sectional view illustrating a portion of a catheter for use with an energy delivery device in accordance with an embodiment of the disclosure.
Figure 8B:
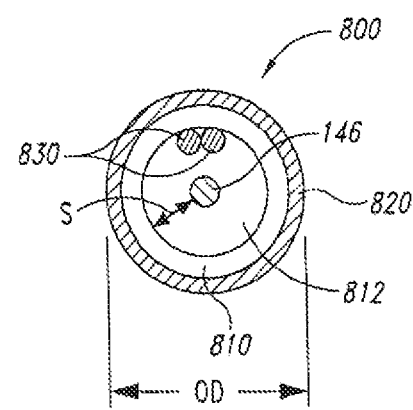

FIGS. 8A and 8B illustrate a specific embodiment of the elongated body 130. In this embodiment, the elongated body 800 includes a coil 810 with a lumen 812 and an outer casing 820 over the coil 810 and fixed at distal and proximal ends. The coil 810 can be a flexible winding of a suitable metal or polymer that can be pushed/pulled in a longitudinal direction, transmit torsional forces, and prevent kinking or collapse of the lumen 812. The casing 820 can be a coating or thicker cover that is also flexible and configured to have an outer diameter "OD" in a range from about 0.75 mm to about 1.6 mm to enable suction and fluid irrigation through a 2 mm working lumen of the access device without catheter removal. The casing 820 can be made from pebax, nylon, grilimide, or other polymeric materials.

The lumen 812 of the coil 810 provides a large space "S" (FIG. 8B) through which the wire 146 and one or more thermocouple leads 830 can extend. The large space S between the wire 146 and the coil 810 reduces friction between the wire 146 and the elongated body 130 such that the wire 146 can readily move longitudinally within the coil 810. This allows the wire 146 to move proximally/distally to move the electrodes 142 outwardly/inwardly along a significant portion of the stroke/trigger length of the actuator of the handle, which may be in a range from about 5 mm to about 40 mm. As a result, the electrodes may be more easily deployed compared to catheters with higher friction between the wire 146 and the elongated body 130. The tactile feedback to the operator is also enhanced with less friction, the trigger handle design, and/or torsional spring such that it is easier for an operator to determine when the electrodes 142 sufficiently contact an airway. The outer diameter OD of the casing 820 can also be relatively small because the elongated body 130 does not include a slideable sheath around an extrusion. Consequently, the elongated body 130 occupies less space in the working lumen of a bronchoscope such that fluids can be extracted/injected into the passageway through the working lumen. For example, a solution or gas can be injected into an airway through the working lumen of a bronchoscope with the elongated body in the working lumen, and alternatively mucus and other matter can be suctioned from the airways via the working lumen of the bronchoscope with the elongated body in the working lumen.

From the foregoing, it will be appreciated that specific embodiments of the invention have been described herein for purposes of illustration, but that various modifications may be made without deviating from the inventions. For example, many of the elements of one embodiment can be combined with other embodiments in addition to, or in lieu of, the elements of the other embodiments. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is inclusive and therefore used throughout to mean including at least the recited feature(s) such that any greater number of the same feature and/or additional types of features are not precluded. Therefore, the invention is not limited except as by the appended claims.

We claim:

1. An energy delivery device, comprising:
   a body having a proximal portion, a distal portion, and a lumen extending along the proximal and distal portions;
   a wire extending through the lumen;
   an energy delivery element at the distal portion of the body and attached to the wire; and
   a handle having a grip, a head coupled to the proximal portion of the body and located at an upper portion of the grip, and an actuator mechanism coupled to the wire, wherein the handle comprises a first portion and a second portion rotatably attached to the first portion, the actuator is defined by one of the first portion and the second portion, the second portion has a flange with a notch and the first portion has a lever pivotally attached to the first portion, and the lever has a first end in the notch and a second end attached to the wire.

2. The energy delivery device of claim 1, wherein the energy delivery element comprises an electrode.

3. The energy delivery device of claim 1, wherein the body comprises a catheter including a cover with an inner wall, a coil coupled to the inner wall of the cover, and a lumen in the coil, and wherein the wire extends through the lumen of the coil.

4. The energy delivery device of claim 1, wherein the head projects outwardly from the grip such that a portion of the grip is narrower than the head.

5. An energy delivery device, comprising:
   a body having a proximal portion, a distal portion, and a lumen extending along the proximal and distal portions;
   a member extending through the lumen;
   an electrode unit at the distal portion of the body attached to the member, and having a plurality of circumferentially spaced electrodes, wherein distal ends of the plurality of circumferentially spaced electrodes converge toward one another; and
   a handle, wherein the member is coupled to a distal end of the electrode unit, wherein the member is configured to move reciprocally relative to the body via actuation of the handle, reciprocal movement of the member is configured to transition the electrode unit between a first, radially-collapsed configuration and a second, radially-expanded configuration, the member is biased in a distal direction by a resilient member or spring disposed proximally of the electrode unit to bias the electrode unit in the first, radially-collapsed configuration, and the electrode unit is transitioned from the first, radially-collapsed configuration to the second, radially-expanded configuration by pulling the member in a proximal direction.

6. The energy delivery device of claim 5, wherein the body comprises a catheter including a cover with an inner wall, a coil coupled to the inner wall of the cover, and a lumen in the coil, and the member extends through the lumen of the coil.

7. The energy delivery device of claim 5, wherein the handle has a first portion and a second portion rotatably attached to the first portion, the proximal portion of the body is coupled to one of the first and second portions, the member is coupled to one of the first and second portions such that relative rotation between the first and second portions moves the member longitudinally along the body, and the first portion has a first curved surface and the second portion has a second curved surface arranged such that the first and second curved surfaces define a hyperbolic-like shaped grip.

8. The energy delivery device of claim 7, wherein the second portion has a flange with a notch and the first portion has a lever pivotally attached to the first portion, and the lever has a first end in the notch and a second end attached to the member.

9. The energy delivery device of claim 5, wherein the resilient member or spring is disposed within the handle.

10. The energy delivery device of claim 5, wherein the electrode unit is transitioned from the second, radially-expanded configuration to the first, radially-collapsed configuration by releasing the member after it is pulled.

11. The energy delivery device of claim 5, wherein the member is a wire.

12. The energy delivery device of claim 5, wherein the electrode unit further includes a distal tip, the distal ends of the plurality of circumferentially spaced electrodes converge toward the distal tip, and the member extends through a volume defined by the plurality of circumferentially spaced electrodes to the distal tip.

13. The energy delivery device of claim 5, further including an energy generator configured to deliver radio frequency energy to the plurality of circumferentially spaced electrodes through the member.

14. An energy delivery device, comprising:
a body having a cover with an inner wall, a coil coupled to the inner wall of the cover, and a lumen in the coil;
a member extending through the lumen;
an energy delivery unit at a distal portion of the body, the energy delivery unit having a proximal retainer fixed to the body, a distal retainer attached to the member, and a plurality of flexible electrodes having proximal ends attached to the proximal retainer and distal ends attached to the distal retainer, wherein the member is coupled to a distal end of the energy delivery unit; and
a handle having a grip, a head coupled to a proximal portion of the body and located at an upper portion of the grip, and an actuator mechanism coupled to the member, wherein the head projects outwardly from the grip such that a portion of the grip is narrower than the head, the member is configured to move reciprocally relative to the body via actuation of the actuator mechanism, reciprocal movement of the member is configured to transition the energy delivery unit between a first, radially-collapsed configuration and a second, radially-expanded configuration, the member is biased in a distal direction by a resilient member or spring disposed proximally of the energy delivery unit to bias the energy delivery unit in the first, radially-collapsed configuration, and the energy delivery unit is transitioned from the first, radially-collapsed configuration to the second, radially-expanded configuration by pulling the member in a proximal direction.

15. The energy delivery device of claim 14, wherein a stroke length of the actuator mechanism of the handle is in a range from about 5 mm to about 40 mm.

16. The energy delivery device of claim 14, wherein the member is a wire.

17. The energy delivery device of claim 14, wherein the energy delivery unit is transitioned from the second, radially-expanded configuration to the first, radially-collapsed configuration by releasing the member after it is pulled.

* * * * *